United States Patent [19]

Brown et al.

[11] Patent Number: 4,837,374
[45] Date of Patent: Jun. 6, 1989

[54] MICROREACTOR FOR ANALYZING THIN SOLID SAMPLES

[76] Inventors: James R. Brown, 22 Milne Crescent, Kanata, Ontario, Canada, K2K 1H8; Leighton L. Coatsworth, 646 Platt's Lane, London, Ontario, Canada, N6G 3B2; Irold S. Schmidt, 857 Farnham Grove, London, Ontario, Canada, N6K 1S5

[21] Appl. No.: 56,126

[22] Filed: Jun. 1, 1987

[51] Int. Cl.[4] .................................................. G01N 31/12
[52] U.S. Cl. ..................................... 422/130; 422/80; 422/78
[58] Field of Search .................. 422/78, 130, 164–167; 436/119–123, 155–160

[56] References Cited

U.S. PATENT DOCUMENTS

| | | | |
|---|---|---|---|
| 3,567,388 | 3/1971 | Kapft | 23/253 |
| 3,647,385 | 3/1972 | Stephens | 23/230 PC |
| 3,703,355 | 11/1972 | Takahashi et al. | 23/230 PC |
| 3,904,366 | 9/1975 | Grasenick | 422/78 |
| 3,972,682 | 8/1976 | Stephens et al. | 422/78 |
| 4,087,249 | 5/1978 | Okumoto et al. | 23/253 PC |
| 4,351,801 | 9/1982 | Bartke | 422/78 |
| 4,352,781 | 10/1982 | O'Brien | 422/78 |
| 4,496,249 | 1/1985 | Lee et al. | 374/7 |
| 4,585,622 | 4/1986 | Bowe et al. | 422/50 |
| 4,666,860 | 5/1987 | Blades et al. | 422/78 |
| 4,710,354 | 12/1987 | Behar et al. | 422/78 |

Primary Examiner—Barry S. Richman
Assistant Examiner—T. J. Wallen

[57] ABSTRACT

A microreactor is described which is especially designed to analyze small solid samples, such as thin film catalyst. It includes (a) a horizontal tubular reaction vessel for receiving an article for testing, one end of the vessel being closed and the other end being connected to a ball valve end flange, (b) a horizontal shelf within the reaction vessel adapted to receive and support the article for testing, (c) gas inlet means for introducing gas into the vessel, (d) gas outlet means for removing gas from the vessel, (e) sensing means for sensing the temperature within the reaction vessel, (f) means disposed outwardly of the vessel and in heat-conductive relation to the outer surface thereof for heating the vessel, and (g) releaseable gripper means for delivering the article for testing through the ball valve and into the reaction vessel and for releasing the article onto the shelf.

5 Claims, 2 Drawing Sheets

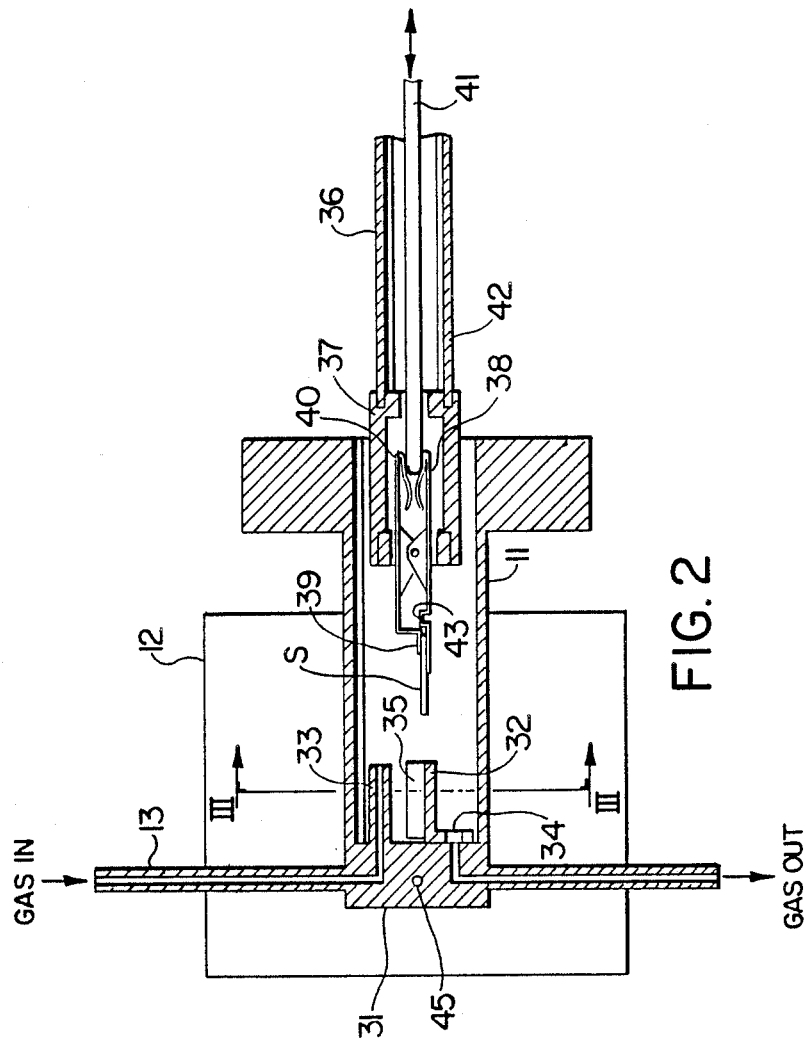

MICROREACTOR FOR ANALYZING THIN SOLID SAMPLES

BACKGROUND OF THE INVENTION

This invention relates to a chemical reaction apparatus and, in particular, to a microreactor for conducting chemical reactions to test solid samples, such as thin film catalysts.

In chemical laboratories, it is often desired to employ microreactors to produce chemical reactions at predetermined temperatures and pressures of small quantities of reactants, sometimes involving catalysts. Small-sized reactions may be desirable for many reasons. For instance, if only small amounts of the reactants or catalysts are available, it may be desired to test their properties before proceeding with their further development. The behaviour of catalysts themselves under varying conditions may be the object of the investigation and microreactors are valuable because they are more easily able to produce desired pressure or temperature changes than are larger test units. The microreactors with their controlled volumes, rates of flow, temperatures, etc. are well-suited to enable scale up of production processes. One such prior microreactor is described in Bowe, et al. U.S. Pat. No. 4,585,622, issued Apr. 20, 1986, which is particularly concerned with regulating the temperature within a reaction tube within tightly controlled limits and being capable of effecting changes of temperature in the reactor tube at high rates of speed. This requires a quite complex temperature sensing and temperature controlling system.

Okumoto, et al. U.S. Pat. No. 4,087,249, issued May 7, 1978, describes a pyrolysis apparatus for analysis in which a connecting rod and sample dish are used for inserting a sample into a reaction tube.

It is the object of the present invention to provide a microreactor especially adapted for analyzing small solid samples, such as thin-film catalysts.

SUMMARY OF THE INVENTION

In accordance with the present invention, a microreactor apparatus is provided having a very small reaction chamber in order to minimize any catalytic effects of the reaction chamber walls themselves. The reaction chamber is in the form of a horizontal tubular vessel for receiving a small, discrete solid sample for testing, one end of the vessel being closed and the other end being connected to a ball valve end flange. A horizontal shelf arrangement within the reaction chamber is adapted to receive and support the solid sample for testing. A gas inlet is positioned for introducing gases into the vessel without disturbing the solid sample and a gas outlet is also provided for removing gaseous products from the vessel. Sensing means are provided for sensing the temperature within the vessel and means are disposed outwardly of the vessel and in heat-conductive relation to the outer surface thereof for heating the vessel. A releaseable gripper means is adapted for delivering the solid sample through the ball valve and into the vessel and for releasing the catalyst sample onto the shelf.

The solid sample for testing is typically in the form of a small, thin disc or chip. While the reactor can be used for testing any type of small, discrete solid sample, it is particularly useful for testing thin film catalyst samples, such as cobalt-molybdenum thin film catalyst samples typically having a thickness of about 0.5 mm and a diameter of about 14–15 mm. Such a sample is very light and it is important that the gas inlet be positioned such that it does not blow the solid sample off the shelf. Preferably, the closed end of the reaction vessel is closed by means of a closure plug and the shelf projects inwardly from the inner face of that plug. The gas inlet passes through the closure plug and includes a tubular portion extending inwardly from the plug into the vessel at least as far as the inner end of the shelf. The gas outlet also extends through the plug and the plug also preferably holds a thermocouple for measuring temperature.

The releaseable gripper means is an important part of the invention and comprises a hollow tubular member with a pair of pivotally mounted arms projecting from one end. The outer ends of these arms have jaws for gripping the catalyst sample and the inner ends of the arms are engageable with an actuating rod extending through the hollow tubular member and being adapted to engage the arms for gripping and releasing a catalyst sample between the jaws. The hollow tubular member and the actuating rod may be attached to a linear motion drive forming part of the introduction chamber of a UHV surface spectrometer. Thus, actuation of the linear motion drive can move a sample from the introduction chamber through the ball valve and into the reaction vessel. When the sample has been deposited on the shelf, the releaseable gripper means is backed out of the reaction vessel and the ball valve is closed for conducting the test.

BRIEF DESCRIPTION OF THE DRAWINGS

Certain preferred features of the present invention are illustrated by the attached drawings:

FIG. 2 is a longitudinal cross-sectional view of the sample cell of the invention; and FIG. 3 is a sectional view along line III—III of FIG. 2.

Figure 1:
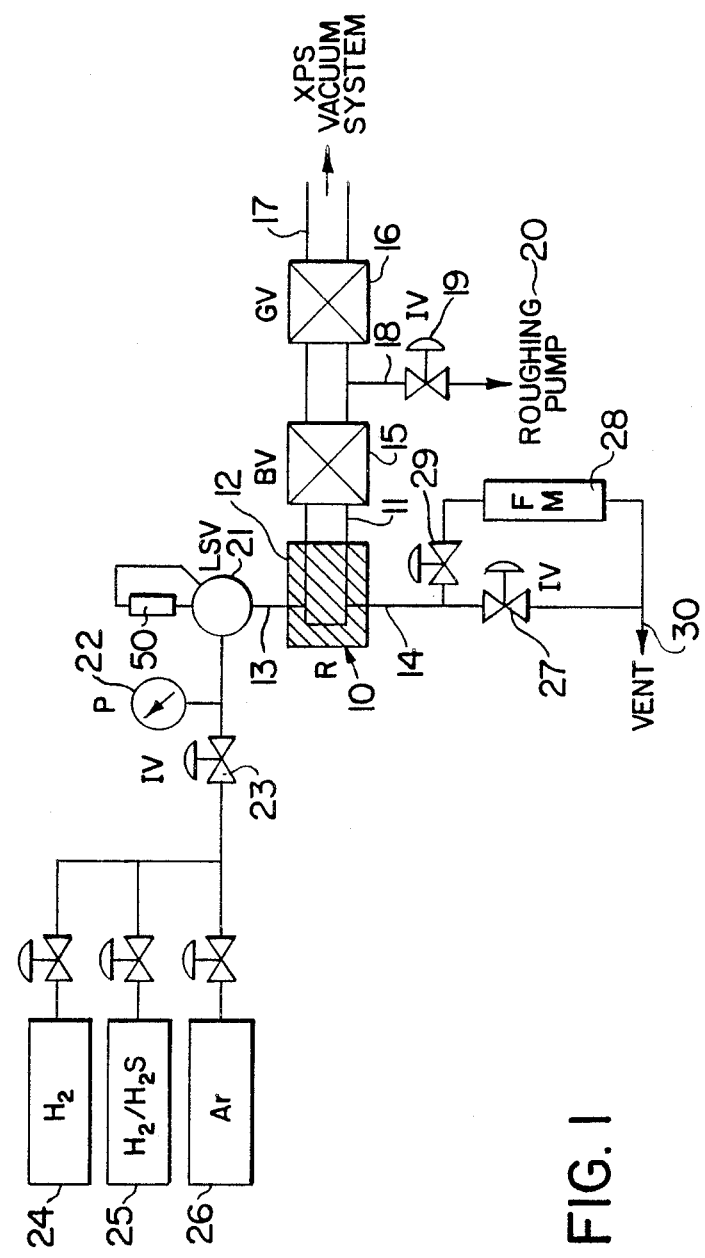
FIG. 1 is a schematic illustration of the apparatus of the invention.

The microreactor apparatus of this invention is designed to allow reactions of thin film model catalyst specimens to be carried out at pressures of up to 10 atmospheres and temperatures of up to 600° C. A main feature of the microreactor is the ability to introduce only the thin film specimen into the reactor. In this way any possible side reactions with the sample holder are minimized.

As seen in FIG. 1, the main reactor unit 10 includes a tubular vessel portion 11 which may conveniently be a stainless steel tube having a diameter of 25.4 mm and a length of 67 mm. One end of this tubular vessel 11 is welded to a water cooled end flange of a ball valve 15. The other end of the hollow vessel 11 is sealed by an end plug 31 welded into the tube. The welds are preferably made using a tungsten inert gas technique with no filler rod material since this could cause contamination as well as premature weld failure especially in the presence of hydrogen at high pressures.

The ball valve 15 may, for example, may be a Model SS-65TSW12P available from the Whitney Company. This valve has a reinforced TFE seat and the body of the valve is made from 316 stainless steel. As a safety precaution, the Viton seal and the TFE seat are cooled by a cooling water channel (not shown) machined into the flange of the ball valve closest to the reactor.

The tubular reactor vessel 11 is partially surrounded by a heater 12 consisting of two half copper blocks bolted to the exterior of the tubular vessel and containing six 100 watt cartridge heaters.

A gas inlet tube 13 feeds into the reactor vessel through end plug 31 and inner tube 33. A gas outlet line 14 connects to the reactor vessel through end plug 31 with outlet opening 34 within the reactor. Projecting inwardly from the inner face of the end plug 31 is the shelf 32 for supporting the catalyst sample S. This shelf 32 consists of a pair of laterally spaced and inwardly projecting L-shaped ledges upon which the sample S rests, the space between the ledges providing access for the gripper jaws. The ledges have side edges 35 to retain the sample in a fixed lateral position.

The gas inlet line 13 connects to a liquid sampling valve 21, as well as a pressure gauge 22 and an isolation valve 23. Connecting through the isolation valve 23 are a source of hydrogen 24, a source of $H_2/H_2S$ 25 and a source of argon 26.

The liquid sampling valve 21 is preferably a gas chromatograph liquid sampling valve Model 14T available from Valco Instruments Company Inc. Liquid reactants held in vessel 50 are injected into the reactor through this valve and it allows 1 $\mu$l of a liquid reactant to be injected into the reactor at an operating pressure of 10 atmospheres.

The gas outlet line 14 connects to an isolation valve 27 and also via a loop connects to valve 29 and flow meter 28 to vent 30.

In order to ensure that the sample introduction system remains absolutely free of any reaction gases as well as to allow an associated spectrometer system to be used while reactions are in progress, a UHV gate valve 16 is placed in series with the ball valve 15. An isolation valve 19 is connected between ball valve 15 and gate valve 16 via line 18 and this connects to a roughing pump 20. With this system, any trace of reactant gases can be removed from the reactor 11 by partially evacuating the system prior to exposure to the introduction system of the spectrometer. The reactor and sample are protected from any backstreaming hydrocarbon contamination from the roughing pump by means of a coaxial foreline trap.

As shown in FIG. 2, the releaseable gripper means includes a tubular member 36 having at one end thereof a gripper support mechanism 37 with a pair of pivotally mounted arms 38 projecting from the end thereof. The outer ends of the arms 38 are in the form of a pair of gripper jaws 39 for holding a sample S for testing. The pivotally mounted arms are spring biased to cause the jaws 39 to separate from each other. The inner ends of arms 38 have inwardly turned flanges 40 forming a recess gap. A push rod 41 is axially mounted within tubular member 36 and slides within a guideway 42. This push rod 41 is adapted to engage the inner flanges 40 of arms 38 such that when the rod 41 is pushed between the flanges 40, the jaws 39 close to grip the sample. When the rod 41 is pulled back and out of engagement with the arms 38, the jaws separate under action of the spring to release the sample.

The outer ends of tubular member 36 is connected to a linear motion drive system of known type, such as Model LMD925, Vacuum Generators Limited, which forms part of the introduction chamber of a UHV surface spectrometer. With this system, a sample for testing is introduced into an introduction chamber supported in a holder. The chamber is then closed and evacuated nd the linear motion drive moves tubular member 36 and jaws 39 into a position with the jaws 39 above and below the sample S. The stop 43 prevents the sample from moving too far inwardly between the jaws 39. The push rod 41 is then moved forwardly relative to tubular member 36 into the position shown in FIG. 2 thereby causing the jaws 39 to clamp the sample therebetween. Next, the tubular member 36 and push rod 41 are moved simultaneously whereby the sample is transferred from the introduction chamber into the reactor vessel 11. The jaws 39 move between the shelf ledges 32 whereby the sample is delivered to a location above the ledges and between the side edges 35. The push rod 41 is then pulled back relative to the tubular member 36 so that it disengages from the flanges 40, permitting the jaws 39 to open whereby the sample is deposited on the shelf ledges 32. The tubular member 36 and push rod 41 are then backed out of vessel 11, ball valve 15 and gate valve 16 so that the valves can be closed for testing of the sample.

After the sample has been tested, the ball valve 15 and gate valve 16 are again opened so that the gripper mechanism can once again move into the tubular reactor vessel 11 to a location with the jaws 39 in an open position between the ledges 32 and above and below the sample. The push rod 41 then moves forward relative to the tubular member 36 to engage the interior flanges 41 thereby causing the jaws 39 to clamp the sample therebetween. The entire gripper mechanism then can be backed out of the system through ball valve 15 and gate valve 16 to return the sample to the introduction chamber. After the sample has been released from the jaws 39, it can either be removed from the introduction chamber for further analysis or it may be transferred directly from the introduction chamber into a spectrometer.

While the invention has been described with respect to certain specific embodiments, it will be appreciated that many modifications and changes may be made by those skilled in the art without departing from the spirit of the invention.

We claim:

1. A reactor apparatus comprising:
    (a) a horizontal tubular reactor vessel for receiving an article for testing, a first end of said vessel being closed and a second end being connected to a ball valve end flange,
    (b) a pair of horizontal laterally spaced shelves within the reactor vessel, said shelves projecting horizontally inwardly from said first closed end and adapted to receive and support the article for testing,
    (c) gas inlet means for introducing gas into the vessel,
    (d) gas outlet means for removing gas from the vessel,
    (e) sensing means for sensing temperatures within the vessel,
    (f) means disposed outwardly of said reactor vessel and in heat-conductive relation to an outer surface thereof for heating said vessel, and
    (g) releasable gripper means for delivering said article for testing through a ball valve and into the reactor vessel and for releasing said article onto said shelves.

2. The reactor apparatus according to claim 1, wherein the closed end of the vessel means is closed by means of a closure plug.

3. The reactor apparatus according to claim 2, wherein the closure plug contains a said gas inlet and a said gas outlet.

4. The reactor apparatus according to claim 2, wherein the closure plug includes a thermocouple for measuring temperature.

5. The reactor apparatus according to claim 1, wherein the releasable gripper means comprises a hollow tubular member with a pair of pivotally mounted arms projecting from one end, outer ends of said arms having jaws for gripping said article for testing and inner ends of the arms being engageable with an actuator rod extending through said hollow tubular member, said actuator rod being adapted to engage the arms for gripping and releasing an article held between the jaws.

* * * * *